US009861121B2

(12) United States Patent
Urazono et al.

(10) Patent No.: US 9,861,121 B2
(45) Date of Patent: Jan. 9, 2018

(54) MILK BASIC PROTEIN COMPOSITION AND PRODUCTION PROCESS THEREFOR

(71) Applicant: MEGMILK SNOW BRAND CO., LTD., Hokkaido (JP)

(72) Inventors: Hiroshi Urazono, Saitama (JP); Yoshikazu Morita, Saitama (JP); Noriko Ueda, Saitama (JP); Hiroshi Ueno, Saitama (JP); Ken Katoh, Saitama (JP); Toshiya Kobayashi, Saitama (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 0 days.

(21) Appl. No.: 14/779,647

(22) PCT Filed: Mar. 25, 2014

(86) PCT No.: PCT/JP2014/058209
§ 371 (c)(1),
(2) Date: Sep. 24, 2015

(87) PCT Pub. No.: WO2014/157156
PCT Pub. Date: Oct. 2, 2014

(65) Prior Publication Data

US 2016/0044949 A1 Feb. 18, 2016

(30) Foreign Application Priority Data

Mar. 28, 2013 (JP) ................................ 2013-070417

(51) Int. Cl.

| | |
|---|---|
| ***A23C 9/146*** | (2006.01) |
| ***A23L 1/305*** | (2006.01) |
| ***A23L 2/66*** | (2006.01) |
| ***A23J 1/20*** | (2006.01) |
| ***A61K 38/01*** | (2006.01) |
| ***A61K 35/20*** | (2006.01) |
| ***A61K 38/30*** | (2006.01) |
| ***A61K 38/40*** | (2006.01) |
| ***A61K 38/44*** | (2006.01) |
| ***A61K 47/24*** | (2006.01) |
| ***A61K 47/36*** | (2006.01) |
| ***A61K 47/38*** | (2006.01) |
| ***A61K 47/42*** | (2017.01) |
| ***A23K 20/147*** | (2016.01) |
| ***A23L 29/10*** | (2016.01) |
| ***A23L 29/20*** | (2016.01) |
| ***A23L 29/231*** | (2016.01) |
| ***A23L 29/262*** | (2016.01) |
| ***A23L 29/269*** | (2016.01) |

(Continued)

(52) U.S. Cl.
CPC ............... *A23L 1/3056* (2013.01); *A23J 1/20* (2013.01); *A23K 20/147* (2016.05); *A23L 2/66* (2013.01); *A23L 29/10* (2016.08); *A23L 29/20* (2016.08); *A23L 29/231* (2016.08); *A23L 29/262* (2016.08); *A23L 29/269* (2016.08); *A23L 29/27* (2016.08); *A23L 29/275* (2016.08); *A23L 33/19* (2016.08); *A61K 35/20* (2013.01); *A61K 38/018* (2013.01); *A61K 38/30* (2013.01); *A61K 38/40* (2013.01); *A61K 38/44* (2013.01); *A61K 47/24* (2013.01); *A61K 47/36* (2013.01); *A61K 47/38* (2013.01); *A61K 47/42* (2013.01); *A23V 2002/00* (2013.01); *A23V 2250/5072* (2013.01); *A23V 2250/5425* (2013.01); *A23V 2250/54248* (2013.01); *A23V 2250/70* (2013.01); *C12Y 111/01007* (2013.01)

(58) Field of Classification Search
CPC .................................................. A23C 9/1465
See application file for complete search history.

(56) References Cited

U.S. PATENT DOCUMENTS

| | | | |
|---|---|---|---|
| 5,543,169 | A | 8/1996 | Colarow et al. |
| 5,976,597 | A | 11/1999 | Takada et al. |
| 2003/0040475 | A1 | 2/2003 | Toba et al. |

(Continued)

FOREIGN PATENT DOCUMENTS

| | | |
|---|---|---|
| EP | 1 228 708 | 8/2002 |
| JP | 9-000163 | 1/1997 |

(Continued)

OTHER PUBLICATIONS

Food and Drug Administration, Overview of Food Ingredients, Additives & Colors, https://www.fda.gov/Food/IngredientsPackagingLabeling/FoodAdditivesIngredients/ucm094211.htm, 2010.*

(Continued)

*Primary Examiner* — Rosanne Kosson

(74) *Attorney, Agent, or Firm* — Greenblum & Bernstein, P.L.C.

(57) ABSTRACT

The present invention provides a protein composition comprising a milk basic protein fraction; and at least one stabilizer selected from the group consisting of soybean polysaccharides, xanthan gum, pectin, gum arabic, gum ghatti, carrageenan, locust bean gum, sodium caseinate, lecithin, and carboxymethylcellulose. The protein composition significantly improves the heat resistance of the milk basic protein fraction. The present invention achieves heat treatment of a protein composition and food, beverage, feed, and pharmaceutical comprising such a protein composition at a temperature exceeding 90° C. without deactivation of the milk basic protein fraction.

19 Claims, No Drawings

(51) Int. Cl.

| | |
|---|---|
| ***A23L 29/275*** | (2016.01) |
| ***A23L 33/19*** | (2016.01) |

(56) References Cited

U.S. PATENT DOCUMENTS

| | | | |
|---|---|---|---|
| 2004/0167078 A1 | 8/2004 | Toba et al. |
| 2010/0298204 A1 | 11/2010 | Serizawa et al. |
| 2015/0064158 A1 | 3/2015 | Katoh et al. |

FOREIGN PATENT DOCUMENTS

| | | |
|---|---|---|
| JP | 9-191856 | 7/1997 |
| JP | 9-238614 | 9/1997 |
| JP | 9-294537 | 11/1997 |
| JP | 11-103788 | 4/1999 |
| JP | 2002-234844 | 8/2002 |
| JP | 2002-281895 | 10/2002 |
| JP | 2004-352669 | 12/2004 |
| JP | 2007-166913 | 7/2007 |
| JP | 2007-246413 | 9/2007 |
| JP | 2007-259733 | 10/2007 |
| JP | 2007-306865 | 11/2007 |
| JP | 2007-330256 | 12/2007 |
| JP | 2010-180219 | 8/2010 |
| WO | 2012/102100 | 8/2012 |

OTHER PUBLICATIONS

Aoe et al., "Controlled Trial of the Effects of Milk Basic Protein (MBP) Supplementation on Bone Metabolism in Healthy Adult Women", *Biosci. Biotechnol. Biochem.* 65(4):913-918, 2001.

International Search Report issued in PCT/JP2014/058209, dated Jun. 17, 2014.

International Preliminary Report on Patentability issued in PCT/JP2014/058209, dated Oct. 8, 2015.

Ueno et al., "Thermal Stability of the Iron-Lactoferrin Complex in Aqueous Solution is Improved by Soluble Soybean Polysaccharide," *Food Biophysics*, vol. 7, No. 3, pp. 183-189, 2012.

Querinjean et al., "Molecular Weight, Single-Chain Structure and Amino Acid Composition of Human Lactoferrin," *Eur. J. Biochem.*, vol. 20, No. 3, pp. 420-425, 1971.

Castellino et al., "Structural Studies on Bovine Lactoferrin," *The Journal of Biological Chemistry*, vol. 245, No. 1, pp. 4269-4275, 1970.

Extended European Search Report issued in EP Patent Application No. 14773646.6, dated Nov. 3, 2016.

* cited by examiner

MILK BASIC PROTEIN COMPOSITION AND PRODUCTION PROCESS THEREFOR

TECHNICAL FIELD

The present invention relates to a protein composition with high heat resistance and to a process for producing the composition. More specifically, the present invention relates to a protein composition with high heat resistance containing a milk basic protein fraction and a stabilizer and to a process for producing the composition.

BACKGROUND ART

Basic protein fractions from milk have been reported to have various physiological functions, such as bone strengthening effect, preventive effect against periodontal diseases, lipid metabolism improving effect, hypotensive effect, stimulatory effect on dermal collagen production, and regulatory effect on the immune system. For effective exploitation of such physiological functions, various foods, beverages, feed, and pharmaceuticals containing a milk basic protein fraction have been developed. Unfortunately, milk basic protein fractions are heat-labile in the neutral pH region and precipitate when heated at a temperature of 80° C. for ten minutes (see, for example, Patent Document 1). For this reason, milk basic protein fraction are generally heated in the acidic pH region. It is reported that such a method can substantially maintain the bone strengthening effect of the milk basic protein fraction even after the heat treatment (see, for example, Non Patent Document 1).

Unfortunately, such a method still involves problems caused by the low thermal stability of the milk basic protein fraction during sterilization at a temperature 90° C. or more, especially retort sterilization, such as: (1) high tendency for aggregation and precipitation of the milk basic protein fraction during thermal sterilization at a temperature 90° C. or more, due to its inadequate heat resistance; and (2) high tendency for deactivation of the milk basic protein fraction during thermal sterilization, particularly under neutral (with a pH value of approximately 7.0) to alkaline conditions. Accordingly, under actual circumstances, it is impossible to employ an extreme heat treatment, such as retort sterilization, in a case of a heat treatment (particularly at a temperature exceeding 90° C.) for a solution containing a milk basic protein fraction, because such a treatment may deactivate the milk basic protein fraction. Such circumstances have been a limitation in blending a milk basic protein fraction in foods, beverages, feed, or pharmaceuticals without deactivating it.

RELATED ART

Patent Document

Patent Document 1: Japanese Patent Application Laid-Open Publication No. 09-191858

Non-Patent Document

Non Patent Document 1: Seiichiro Aoe et al., Bioscience Biotechnology and Biochemistry, 65(4), 913-918 (2001)

DETAILED DESCRIPTION OF THE INVENTION

Summary of Invention

An object of the present invention is to provide a protein composition which can be heated at a temperature of 90° C. or higher without deactivating the milk basic protein fraction contained therein, and a process for producing the composition.

Solution to Problem

The present invention provides the following aspects:

Aspect [1]. A thermally stable protein composition containing: a milk basic protein fraction; and at least one stabilizer selected from the group consisting of soybean polysaccharides, xanthan gum, pectin, gum arabic, gum ghatti, carrageenan, locust bean gum, sodium caseinate, lecithin, and carboxymethylcellulose.

Aspect [2]. The protein composition according to Aspect [1], wherein the milk basic protein fraction has an amino acid composition containing 15% by weight or more basic amino acids.

Aspect [3]. The protein composition according to Aspect [1], wherein:

1) the milk basic protein fraction contains several proteins each having a molecular weight within the range of 3,000 to 80,000 as determined by sodium dodecyl sulfate-polyacrylamide gel electrophoresis (SDS-PAGE);

2) the milk basic protein fraction contains 95% by weight or more proteins and small amounts of lipids and ash;

3) the proteins mainly contained in the milk basic protein fraction are lactoferrin and lactoperoxidase; and 4) the proteins in the milk basic protein fraction have an amino acid composition containing 15% by weight or more basic amino acids.

Aspect [4]. Food, beverage, feed or pharmaceutical containing the protein composition according to any one of Aspects [1] to [3].

Aspect [5]. A process for heat treatment of a milk basic protein fraction including: mixing the milk basic protein fraction with at least one stabilizer selected from the group consisting of soybean polysaccharides, xanthan gum, pectin, gum arabic, gum ghatti, carrageenan, locust bean gum, sodium caseinate, lecithin, and carboxymethylcellulose; and heating the mixture at a temperature of 90° C. or higher.

Aspect [6]. The process for heat treatment of a milk basic protein fraction according to Aspect [5], wherein the milk basic protein fraction has an amino acid composition containing 15% by weight or more basic amino acids.

Aspect [7]. The process for heat treatment of a milk basic protein fraction according to Aspect [5], wherein 1) the milk basic protein fraction contains several proteins each having a molecular weight within the range of 3,000 to 80,000 as determined by sodium dodecyl sulfate-polyacrylamide gel electrophoresis (SDS-PAGE);

2) the milk basic protein fraction contains 95% by weight or more proteins and small amounts of lipids and ash;

3) the proteins mainly contained in the milk basic protein fraction are lactoferrin and lactoperoxidase; and 4) the proteins in the milk basic protein fraction have an amino acid composition containing 15% by weight or more basic amino acids.

Effects of Invention

According to the present invention, a protein composition can be heated at a temperature exceeding 90° C. without deactivation of the milk basic protein fraction contained therein.

DESCRIPTION OF EMBODIMENTS

The present inventors have conducted extensive research on stabilization of milk basic protein fractions against thermal deactivation in order to solve the problems, and have consequently found that a protein composition containing a milk basic protein fraction and a stabilizer, such as soybean polysaccharide or xanthan gum, exhibit significantly high heat resistance. The inventors thus have accomplished the present invention.

Specifically, the protein composition according to an embodiment of the present invention contains a milk basic protein fraction; and at least one stabilizer selected from the group consisting of soybean polysaccharides, xanthan gum, pectin, gum arabic, gum ghatti, carrageenan, locust bean gum, sodium caseinate, lecithin, and carboxymethylcellulose. The protein composition has high heat resistance in a broader pH range extending from acidic to neutral and alkaline pH regions, even during a high-temperature heat treatment at a temperature exceeding 90° C. and during a retort sterilization treatment at a temperature exceeding 120° C.

The milk basic protein fraction preferably has an amino acid composition containing 15% by weight or more basic amino acids. Milk basic protein fractions from any source may be used. For example, milk basic proteins which have the following properties and are known to have bone strengthening effect can be heated at a temperature exceeding 90° C. without being deactivated:

1) the milk basic protein fraction contains several proteins each having a molecular weight within the range of 3,000 to 80,000 as determined by sodium dodecyl sulfate-polyacrylamide gel electrophoresis (SDS-PAGE);

2) the milk basic protein fraction contains 95% by weight or more proteins and small amounts of lipids and ash;

3) the proteins mainly contained in the milk basic protein fraction are lactoferrin and lactoperoxidase; and 4) the proteins in the milk basic protein fraction have an amino acid composition containing 15% by weight or more basic amino acids of milk.

Examples of the basic amino acid of milk include lysine, histidine, and arginine.

The aforementioned basic protein fraction can be prepared by, for example, putting a milk raw material, such as skim milk or whey, into contact with a cation exchange resin so that the basic protein is adsorbed on the resin, eluting the adsorbed basic protein fraction with an eluent having a salt concentration of 0.1M to 1M, recovering the eluted fraction, desalting and concentrating the recovered fraction by reverse osmosis (RO) or electrodialysis (ED), and optionally drying the resultant. Examples of the source of the milk raw material include bovine, buffalo, human, porcine, ovine, caprine, and equine milk.

Examples of known methods for preparing the milk basic protein fraction include: a method by putting milk or a raw material derived from milk into contact with a cation exchanger so that the basic protein in the milk is adsorbed on the cation exchanger, and then eluting the adsorbed milk basic protein fraction with an eluent having a pH value greater than 5 and anionic strength greater than 0.5 (Japanese Patent Application Laid-Open Publication No. H05-202098); a method using an alginate gel (Japanese Patent Application Laid-Open Publication No. S61-246198); a method of separating a basic protein fraction from whey using porous inorganic particles (Japanese Patent Application Laid-Open Publication No. H01-86839); and a method of obtaining a milk basic protein fraction using a sulfated ester compound (Japanese Patent Application Laid-Open Publication No. S63-255300). In the present invention, milk basic protein fraction prepared by such methods may be used.

The main component of the stabilizer preferably has the following characteristics:

(1) The main component has a high molecular weight and film-forming property. Examples of such a component are soybean polysaccharides;

(2) The main component has a high ratio of side chains to the main chain. An example of such a component is xanthan gum that has a glucose main chain to which mannose and glucuronic acid link;

(3) The main component is pectin composed of a galacturonic acid main chain and multiple side chains of galactose, arabinose, or xylose bonded to the main chain;

(4) The main component has a high ratio of side chains to the main chain. An example of such a component is gum arabic that has a galactose main chain to which arabinose and glucuronic acid link.

Stabilizers having such properties prevent deactivation of milk basic protein fraction due to aggregation and precipitation during heating, and thus increase the heat resistance of the milk basic protein fraction.

In contrast, stabilizers having the following properties are not preferred for the composition containing basic proteins of milk:

(1) The stabilizer has hydrophobic and hydrophilic groups and exhibits multilayer adsorption. Examples of such stabilizers are sucrose fatty acid esters that result from the reaction of hydroxyl groups of sucrose with fatty acids; and (2) The stabilizer has a linear structure, such as gellan gum, or has a low ratio of side chains to the main chain. Examples of such stabilizers are guar gum and tamarind gum.

Although use of such stabilizers does not significantly increase the heat resistance of the milk basic protein fraction during heating, the composition may partly contain such stabilizers.

On the basis of these facts, examples of the preferred stabilizer to be mixed with a milk basic protein fraction to prepare a composition containing a basic protein of milk include soybean polysaccharides, xanthan gum, pectin, gum arabic, gum ghatti, carrageenan, locust bean gum, sodium caseinate, lecithin, and carboxymethylcellulose. At least one of these stabilizers is mixed with a milk basic protein fraction to prepare a composition containing a basic protein of milk. Some of these stabilizers have various functions, such as an emulsifying function, but can be used without any problem.

The protein composition may contain the milk basic protein fraction and the stabilizer at any ratio, and preferably contains the stabilizer at a ratio of 0.5 to 100 (weight/weight), more preferably 1 to 40 (weight/weight), with respect to the milk basic protein fraction.

The protein composition may be prepared by any process. For example, if the protein composition is prepared in the form of solution, a milk basic protein fraction and a stabilizer are separately suspended or dissolved in deionized water, and the separate solutions are then mixed by stirring and formed into a food, beverage, feed, or pharmaceutical. The milk basic protein fraction and the stabilizer may be well mixed by stirring under any conditions. They may be mixed by stirring with an ultrasonic disperser while they are being heated to a temperature of approximately 40° C. to 80° C., if necessary. The resulting solution of the protein composition may further be subjected to a process such as concentration with a UF membrane, or lyophilization, if necessary, in order to facilitate the use of the composition for a food, beverage, feed or pharmaceutical.

The protein composition has high thermal stability over a broad pH range extending from acidic to neutral and alkaline pH regions, and thus can endure a high-temperature heat treatment and retort sterilization treatment that are normally employed in the production of foods, beverages, feed and pharmaceuticals. The protein composition in powder form can also endure dry heat sterilization. Accordingly, the protein composition can be used to prepare a food, beverage, feed, or pharmaceutical in various forms such as liquid, gel, powder, and granular forms.

The pH value of the protein composition can be adjusted with an inorganic acid, for example, hydrochloric acid or phosphoric acid; an organic acid, for example, citric acid or acetic acid; or an alkaline agent, for example, sodium hydroxide or sodium hydrogen carbonate. If the protein composition is placed in an environment at a pH value which allows the protein composition to maintain its thermal stability, the protein composition can be subjected to a high-temperature heat treatment or retort sterilization treatment without adjustment of the pH value. The conditions of heat sterilization and the pH value can be appropriately selected depending on the required quality for the intended food, beverage, feed, or pharmaceutical containing the protein composition.

The protein composition may be used for food, beverage, feed, or pharmaceutical, either alone or optionally in the form of a mixture with other raw materials which are normally contained in such products, such as saccharides, lipids, or flavorings.

The present invention will now be described in more details by way of Reference Examples, Examples, and Test Examples which are merely illustrative of embodiments of the invention and are not meant to limit the invention in any way.

Reference Example 1

Preparation of Milk Basic Protein Fraction 1

A column (with a diameter of 5 cm and a length of 30 cm) packed with 400 g of sulfonated Chitopearl (manufactured by Fuji-Spinning Co., Ltd.) as a cation exchange resin was washed thoroughly with deionized water, and then was loaded with 40 liter of unsterilized skim milk (with a pH value of 6.7) at a flow rate of 25 ml/min. The column was then washed thoroughly with deionized water, and the basic protein fraction adsorbed onto the resin was eluted with a 0.02M carbonate buffer (with a pH value of 7.0) containing 0.98M sodium chloride. The eluate was desalted and concentrated with a reverse osmotic (RO) membrane, and the resultant was lyophilized, thereby yielding 21 g of a basic protein fraction in powder form (Reference Example Product A). The milk basic protein fraction thus prepared was measured by sodium lauryl sulfate-polyacrylamide gel electrophoresis (SDS-PAGE). The results revealed that the milk basic protein fraction had a molecular weight ranging from 3,000 to 80,000 and had a composition as shown in Table 1. The milk basic protein fraction was also hydrolyzed with 6N hydrochloric acid at 110° C. for 24 hours, and then was analyzed for the amino acid composition with an amino acid analyzer (L-8500, manufactured by Hitachi, Ltd.). The results are shown in Table 2. The milk basic protein fraction was further analyzed for its protein components by ELISA. Table 3 shows that the milk basic protein fraction contains more than 40% lactoferrin and lactoperoxidase.

TABLE 1

| | |
|---|---|
| Water | 1.06 (% by weight) |
| Proteins | 96.50 |
| Lipids | 0.56 |
| Ash | 0.27 |
| Others | 1.61 |

TABLE 2

| | |
|---|---|
| Aspartic acid | 10.1 (% by weight) |
| Serine | 5.3 |
| Glutamic acid | 12.3 |
| Proline | 4.7 |
| Alanine | 5.7 |
| Leucine | 10.2 |
| Lysine | 8.4 |
| Histidine | 2.5 |
| Arginine | 7.2 |
| Others | 33.6 |

TABLE 3

| | |
|---|---|
| Lactoferrin | 42.5 (% by weight) |
| Lactoperoxidase | 45.6 |
| Insulin-like growth factor-I | 0.005 |
| Others | 11.895 |

Reference Example 2

Preparation of Milk Basic Protein Fraction 2

A column (with a diameter of 100 cm and a length of 10 cm) packed with 30 kg of SP Toyopearl (manufactured by TOSOH CORPORATION) as a cation exchange resin was washed thoroughly with deionized water, and then was loaded with 3 t of cheese whey (with a pH value of 6.2) that had been heat-sterilized at a temperature of 121° C. for 30 seconds at a flow rate of 10 L/min. The column was then washed thoroughly with deionized water, and the basic protein fraction adsorbed onto the resin was eluted with a 0.1M citrate buffer (with a pH value of 5.7) containing 0.9M sodium chloride. The eluate was desalted and concentrated by electrodialysis (ED), and the resultant was lyophilized, thereby yielding 183 g of milk basic protein fraction in powder form (Reference Example Product B).

Test Example 1

The milk basic protein fraction of Reference Example Product A was dissolved in deionized water into a concentration of 100 mg % (Solution A), and 0.2% by weight of soybean polysaccharide as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 50° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As the reference, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation.

In order to determine the degree of degradation of the milk basic protein fraction after the heat treatment, each of the samples and reference samples after the heat treatment was subjected to polyacrylamide gel electrophoresis (SDS-PAGE) to analyze the band pattern of the milk basic protein fraction as described below.

SDS-PAGE: each sample (15 μl) was diluted with 15 μl of sample buffer (containing 1.25 ml of 0.5M Tris-HCl (with a pH value of 6.8), 1.0 ml of glycerol, 2.0 ml of 10% SDS, 0.5 ml of 2-mercaptoethanol, and 0.25 ml of 0.1% BPB), and the resulting solution was heated at a temperature of 100° C. for five minutes. After the heat treatment, each sample (15 μl) was subjected to electrophoresis with 14% polyacrylamide gel (TEFCO SDS-PAGE mini). Kaleidoscope Prestained Standards (BioRad) were used as molecular weight markers. The results are shown in Table 4.

TABLE 4

| | Temperature (° C.) | Evaluation | pH 1 | 2 | 3 | 4 | 5 | 6 | 7 | 8 | 9 | 10 |
|---|---|---|---|---|---|---|---|---|---|---|---|---|
| Protein Composition | 90 | Visual | ± | − | − | − | − | − | − | − | − | ± |
| (milk basic protein | | SDS-PAGE | x | ○ | ○ | ○ | ○ | ○ | ○ | ○ | ○ | Δ |
| fraction + soybean | 100 | Visual | ± | − | − | − | − | − | − | − | − | + |
| polysaccharide) | | SDS-PAGE | x | ○ | ○ | ○ | ○ | ○ | ○ | ○ | ○ | x |
| | 110 | Visual | + | − | − | − | − | − | − | − | − | + |
| | | SDS-PAGE | x | ○ | ○ | ○ | ○ | ○ | ○ | ○ | ○ | x |
| | 120 | Visual | + | − | − | − | − | − | − | − | − | + |
| | | SDS-PAGE | x | ○ | ○ | ○ | ○ | ○ | ○ | ○ | ○ | x |
| | 130 | Visual | + | − | − | − | − | − | − | − | − | + |
| | | SDS-PAGE | x | Δ | ○ | ○ | ○ | ○ | ○ | ○ | Δ | x |
| Control | 110 | Visual | ± | − | − | − | ± | + | + | + | + | + |
| | | SDS-PAGE | x | x | x | x | x | x | x | x | x | x |

Note) 1: visual observation of aggregation and precipitation
"−" indicates transparent due to no aggregation or precipitation.
"±" indicates translucent, but no aggregation or precipitation.
"+" indicates presence of aggregation or precipitation.
Note) 2: observation by electrophoresis (SDS-PAGE)
"○" indicates observation of protein bands by SDS-PAGE.
"Δ" indicates observation of slight protein bands by SDS-PAGE.
"x" indicates observation of no protein band by SDS-PAGE.

The results shown in Table 4 indicate that no aggregation or precipitation was visually observed and bands of the milk basic protein fraction were found by SDS-PAGE for the solutions containing the protein composition composed of basic proteins of milk and soybean polysaccharide at pH values of 2 to 9. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 2 to 9, no aggregation or precipitation was observed and bands of the milk basic protein fraction were found even after the heat treatment at a temperature of 120° C. for ten minutes. These experimental results clearly indicate that the protein composition can retain the milk basic protein fraction without deactivation even after a retort sterilization treatment. In contrast, no band of the milk basic protein fraction was found in the solution containing the milk basic protein fraction alone at pH values of 2 to 9. The results indicate that the milk basic protein fraction had lost its function as a result of thermal denaturation and degradation.

Test Example 2

The milk basic protein fraction of Reference Example Product B was dissolved in deionized water into a concentration of 100 mg % (Solution A), and 0.04% (by weight) of xanthan gum as a stabilizer was dissolved in deionized water (Solution B). The Solutions A and B were mixed together by stirring with an ultrasonic disperser (ULTRA-TURRAX T-25; manufactured by IKA Japan) at 9500 rpm and at a temperature of 50° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1. The results are shown in Table 5.

TABLE 5

| | Temperature (° C.) | Evaluation | pH 1 | 2 | 3 | 4 | 5 | 6 | 7 | 8 | 9 | 10 |
|---|---|---|---|---|---|---|---|---|---|---|---|---|
| Protein Composition (milk basic protein fraction + xanthan gum) | 90 | Visual | + | − | − | − | − | − | − | − | − | ± |
| | | SDS-PAGE | x | ○ | ○ | ○ | ○ | ○ | ○ | ○ | ○ | x |
| | 100 | Visual | + | − | − | − | − | − | − | − | − | + |
| | | SDS-PAGE | x | ○ | ○ | ○ | ○ | ○ | ○ | ○ | ○ | x |
| | 110 | Visual | + | − | − | − | − | − | − | − | − | + |
| | | SDS-PAGE | x | ○ | ○ | ○ | ○ | ○ | ○ | ○ | ○ | x |
| | 120 | Visual | + | − | − | − | − | − | − | − | − | + |
| | | SDS-PAGE | x | ○ | ○ | ○ | ○ | ○ | ○ | ○ | ○ | x |
| | 130 | Visual | + | ± | − | − | − | − | − | − | − | + |
| | | SDS-PAGE | x | ○ | ○ | ○ | ○ | ○ | ○ | ○ | Δ | x |
| Control | 110 | Visual | ± | − | − | − | ± | + | + | + | + | + |
| | | SDS-PAGE | x | x | x | x | x | x | x | x | x | x |

Note) 1: visual observation of aggregation and precipitation
"−" indicates transparent due to no aggregation or precipitation.
"±" indicates translucent, but no aggregation or precipitation.
"+" indicates presence of aggregation or precipitation.
Note) 2: observation by electrophoresis (SDS-PAGE)
"○" indicates observation of protein bands by SDS-PAGE.
"Δ" indicates observation of slight protein bands by SDS-PAGE.
"x" indicates observation of no protein band by SDS-PAGE.

The results shown in Table 5 indicate that no aggregation or precipitation was visually observed and bands of the milk basic protein fraction were found by SDS-PAGE for the solutions containing the protein composition containing the milk basic protein fraction and xanthan gum at pH values of 2 to 9. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 2 to 9, no aggregation or precipitation was observed and bands of the milk basic protein fraction were found even after the heat treatment at a temperature of 130° C. for ten minutes. These experimental results clearly indicate that the protein composition can sufficiently retain the activity of the milk basic protein fraction even after a retort sterilization treatment.

Test Example 3

The milk basic protein fraction of Reference Example Product A was dissolved in deionized water into a concentration of 100 mg % (Solution A), and 0.2% by weight of pectin as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1. The results are shown in Table 6.

TABLE 6

| | Temperature (° C.) | Evaluation | pH 1 | 2 | 3 | 4 | 5 | 6 | 7 | 8 | 9 | 10 |
|---|---|---|---|---|---|---|---|---|---|---|---|---|
| Protein Composition (milk basic protein fraction + pectin) | 90 | Visual | + | ± | ± | − | − | − | − | − | − | ± |
| | | SDS-PAGE | x | ○ | ○ | ○ | ○ | ○ | ○ | ○ | ○ | x |
| | 100 | Visual | + | ± | ± | − | − | − | − | − | − | + |
| | | SDS-PAGE | x | ○ | ○ | ○ | ○ | ○ | ○ | ○ | ○ | x |
| | 110 | Visual | + | ± | ± | − | − | − | − | − | ± | + |
| | | SDS-PAGE | x | Δ | ○ | ○ | ○ | ○ | ○ | ○ | ○ | x |
| | 120 | Visual | + | ± | ± | − | − | − | − | − | ± | + |
| | | SDS-PAGE | x | Δ | ○ | ○ | ○ | ○ | ○ | ○ | Δ | x |
| | 130 | Visual | + | ± | ± | − | − | − | − | − | ± | + |
| | | SDS-PAGE | x | Δ | Δ | ○ | ○ | ○ | ○ | ○ | Δ | x |

TABLE 6-continued

| | Temperature | | pH | | | | | | | | | |
|---|---|---|---|---|---|---|---|---|---|---|---|---|
| | (° C.) | Evaluation | 1 | 2 | 3 | 4 | 5 | 6 | 7 | 8 | 9 | 10 |
| Control | 110 | Visual | ± | – | – | – | ± | + | + | + | + | + |
| | | SDS-PAGE | x | x | x | x | x | x | x | x | x | x |

Note) 1: visual observation of aggregation and precipitation
"–" indicates transparent due to no aggregation or precipitation.
"±" indicates translucent, but no aggregation or precipitation.
"+" indicates presence of aggregation or precipitation.
Note) 2: observation by electrophoresis (SDS-PAGE)
"○" indicates observation of protein bands by SDS-PAGE.
"Δ" indicates observation of slight protein bands by SDS-PAGE.
"x" indicates observation of no protein band by SDS-PAGE.

The results shown in Table 6 indicate that no aggregation or precipitation was visually observed and bands of the milk basic protein fraction were found by SDS-PAGE for the solutions containing the protein composition containing the milk basic protein fraction and pectin at pH values of 2 to 9. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 2 to 9, no aggregation or precipitation was observed and bands of the milk basic protein fraction were found even after the heat treatment at a temperature of 120° C. for eight minutes. These experimental results clearly indicate that the protein composition can sufficiently retain the activity of the milk basic protein fraction even after a retort sterilization treatment.

Test Example 4

The milk basic protein fraction of Reference Example Product B was dissolved in deionized water into a concentration of 100 mg % (Solution A), and 0.1% by weight of gum arabic as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 4 indicate that no aggregation or precipitation was visually observed and bands of the milk basic protein fraction were found by SDS-PAGE for the solutions containing the protein composition containing the milk basic protein fraction and gum arabic at pH values of 3 to 5. Such results demonstrate that the protein composition has very high thermal stability in the acidic pH region. Each sample was also heated for a longer time period to observe the milk basic protein fraction after the heat treatment. For the samples having pH values of 3 to 5, no aggregation or precipitation was observed and bands of the milk basic protein fraction were found even after the heat treatment at a temperature of 120° C. for seven minutes. These experimental results clearly indicate that the protein composition can sufficiently retain the activity of the milk basic protein fraction even after a retort sterilization treatment.

Test Example 5

The milk basic protein fraction of Reference Example Product A was dissolved in deionized water into a concentration of 100 mg % (Solution A), and 0.1% by weight of gum ghatti as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for four minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 5 indicate that no aggregation or precipitation was visually observed and bands of the milk basic protein fraction were found by SDS-PAGE for the solutions containing the protein composition containing the milk basic protein fraction and gum ghatti at pH values of 3 to 8. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 3 to 8, no aggregation or precipitation was observed and bands of the milk basic protein fraction were found even after the heat treatment at a temperature of 120° C. for seven minutes. These experimental results clearly indicate that the protein composition can sufficiently retain the activity of the milk basic protein fraction even after a retort sterilization treatment.

Test Example 6

The milk basic protein fraction of Reference Example Product B was dissolved in deionized water into a concentration of 100 mg % (Solution A), and 0.2% by weight of carrageenan as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 6 indicate that no aggregation or precipitation was visually observed and bands of the milk basic protein fraction were found by SDS-PAGE for the solutions containing the protein composition containing the milk basic protein fraction and carrageenan at pH values of 4 to 8. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 4 to 8, no aggregation or precipitation was observed and bands of the milk basic protein fraction were found even after the heat treatment at a temperature of 120° C. for six minutes. These experimental results clearly indicate that the protein composition can sufficiently retain the activity of the milk basic protein fraction even after a retort sterilization treatment.

Test Example 7

The milk basic protein fraction of Reference Example Product A was dissolved in deionized water into a concentration of 100 mg % (Solution A), and 0.15% by weight of locust bean gum as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 7 indicate that no aggregation or precipitation was visually observed and bands of the milk basic protein fraction were found by SDS-PAGE for the solutions containing the protein composition containing the milk basic protein fraction and locust bean gum at pH values of 4 to 7. Such results demonstrate that the protein composition is stable at the acidic pH region and has very high thermal stability in the neutral pH region. Each sample was also heated for a longer time period to observe the milk basic protein fraction after the heat treatment. For the samples having pH values of 4 to 7, no aggregation or precipitation was observed and bands of the milk basic protein fraction were found even after the heat treatment at a temperature of 120° C. for five minutes. These experimental results clearly indicate that the protein composition can sufficiently retain the activity of the milk basic protein fraction even after a retort sterilization treatment.

Test Example 8

The milk basic protein fraction of Reference Example Product B was dissolved in deionized water into a concentration of 100 mg % (Solution A), and 0.15% by weight of sodium caseinate as a stabilizer was dissolved in deionized water (Solution B). The Solutions A and B were mixed together by stirring with an ultrasonic disperser (ULTRA-TURRAX T-25; manufactured by IKA Japan) at 9500 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 8 indicate that no aggregation or precipitation was visually observed and bands of the milk basic protein fraction were found by SDS-PAGE for the solutions containing the protein composition containing the milk basic protein fraction and sodium caseinate at pH values of 5 to 9. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 5 to 9, no aggregation or precipitation was observed and bands of the milk basic protein fraction were found even after the heat treatment at a temperature of 120° C. for five minutes. These experimental results clearly indicate that the protein composition can sufficiently retain the activity of the milk basic protein fraction even after a retort sterilization treatment.

Test Example 9

The milk basic protein fraction of Reference Example Product A was dissolved in deionized water into a concentration of 100 mg % (Solution A), and 0.25% by weight of lecithin as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 9 indicate that no aggregation or precipitation was visually observed and bands of the milk basic protein fraction were found by SDS-PAGE for the solutions containing the protein composition containing the milk basic protein fraction and lecithin at pH values of 3 to 8. Such results demonstrate that the protein composition is stable at the acidic pH region and has very high thermal stability in the neutral and alkaline pH regions. Each sample was also heated for a longer time period to observe the milk basic protein fraction after the heat treatment. For the samples having pH values of 3 to 8, no aggregation or precipitation was observed and bands of the milk basic protein fraction were found even after the heat treatment at a temperature of 120° C. for six minutes. These experimental results clearly indicate that the protein composition can sufficiently retain the activity of the milk basic protein fraction even after a retort sterilization treatment.

Test Example 10

The milk basic protein fraction of Reference Example Product B was dissolved in deionized water into a concentration of 100 mg % (Solution A), and 0.15% by weight of carboxymethylcellulose as a stabilizer was dissolved in deionized water (Solution B). The Solutions A and B were mixed together by stirring with an ultrasonic disperser (ULTRA-TURRAX T-25; manufactured by IKA Japan) at 8000 rpm and at a temperature of 40° C. for three minutes to prepare a protein composition. Lactic acid or sodium hydroxide solution was then added to the protein composition as pH adjusters, to prepare ten samples having pH values of 1 to 10, respectively. Each sample (2 ml) was dispensed in ampules, and was heated for four minutes at temperatures of 90° C., 100° C., 110° C., 120° C., or 130° C. As controls, the solutions which contained the milk basic protein fraction but did not contain any stabilizer (i.e. solution A) were adjusted to have pH values as described above, and the resulting samples were heated at a temperature of 110° C. for four minutes. Each of the samples and control samples after the heat treatment was visually analyzed for aggregation and precipitation. In order to determine the degree of degradation of the milk basic protein fraction after the heat treatment, each of the samples and control samples after the heat treatment was subjected to polyacrylamide gel electrophoresis (SDS-PAGE) to analyze the band pattern of the milk basic protein fraction as in Test Example 1.

The results of Test Example 10 indicate that no aggregation or precipitation was visually observed and bands of the milk basic protein fraction were found by SDS-PAGE for the solutions containing the protein composition containing the milk basic protein fraction and carboxymethylcellulose at pH values of 3 to 7. Such results demonstrate that the protein composition is stable at the acidic pH region and has very high thermal stability in the neutral pH region. Each sample was also heated for a longer time period to observe the milk basic protein fraction after the heat treatment. For the samples having pH values of 3 to 7, no aggregation or precipitation was observed and bands of the milk basic protein fraction were found even after the heat treatment at a temperature of 120° C. for six minutes. These experimental results clearly indicate that the protein composition can sufficiently retain the activity of the milk basic protein fraction even after a retort sterilization treatment.

Test Example 11

Each of the samples prepared in Test Examples 1 to 10 was adjusted to have a pH value of 7 and was heated at a temperature of 140° C. for five minutes. Each of the samples was then analyzed for the antigenicity by ELISA using antibodies against the milk basic protein fraction. As a control, the milk basic protein fraction not mixed with any stabilizer was heated at a temperature of 140° C. for five minutes, and then was reacted with the antibody. The reactivity observed for the control was set as 1. The reactivity of each protein composition with the antibody was calculated as a relative value to that of the control. The results are shown in Table 7.

TABLE 7

| Stabilizers contained in the respective protein compositions | Relative reactivity of the milk basic protein fraction with the antibody |
|---|---|
| Control | 1.00 ± 0.35 |
| Soybean polysaccharide | 6.05 ± 0.76 a |
| Xanthan gum | 11.32 ± 0.98 a |
| Pectin | 19.35 ± 0.86 a |
| Gum arabic | 3.21 ± 0.55 a |
| Gum ghatti | 2.63 ± 0.51 a |
| Carrageenan | 12.59 ± 0.83 a |

TABLE 7-continued

| Stabilizers contained in the respective protein compositions | Relative reactivity of the milk basic protein fraction with the antibody |
|---|---|
| Locust bean gum | 9.57 ± 0.67 a |
| Sodium caseinate | 2.47 ± 0.60 a |
| Lecithin | 9.47 ± 0.84 a |
| Carboxymethylcellulose | 2.05 ± 0.38 a |

The reactivity is represented by a relative value to that of the milk basic protein fraction alone with the antibody (set as 1).
The numeric value indicates mean ± standard deviation (n = 6).
"a" indicates a significant difference from the reactivity of the control ($p < 0.05$).

The results shown in Table 7 revealed that all the protein compositions maintained relative reactivities with the antibody of 1 or greater with respect to that observed for the milk basic protein fraction alone after the heating up to a temperature of 140° C. Such results demonstrate that the protein composition of the present invention is stable against an extreme heat treatment at a temperature of 140° C.

Test Example 12

Each of the samples prepared in Test Examples 1 to 10 was adjusted to have a pH value of 7 and was heated at a temperature of 140° C. for five minutes. Each of the samples was then measured for the osteoblast proliferation activity. As a control, the milk basic protein fraction not mixed with any stabilizer was heated at a temperature of 140° C. for five minutes, and then was measured for the osteoblast proliferation activity (set as 1). The osteoblast proliferation activity of each protein composition is shown in Table 8 as a relative value to that of the control.

TABLE 8

| Stabilizers contained in the respective protein compositions | Relative osteoblast proliferation activity |
|---|---|
| Control | 1.00 ± 0.08 |
| Soybean polysaccharide | 1.37 ± 0.10 a |
| Xanthan gum | 1.95 ± 0.09 a |
| Pectin | 1.62 ± 0.16 a |
| Gum arabic | 1.16 ± 0.08 a |
| Gum ghatti | 1.24 ± 0.12 a |
| Carrageenan | 1.21 ± 0.07 a |
| Locust bean gum | 1.18 ± 0.10 a |
| Sodium caseinate | 1.85 ± 0.14 a |
| Lecithin | 1.44 ± 0.21 a |
| Carboxymethylcellulose | 1.56 ± 0.22 a |

The osteoblast proliferation activity value is represented by a relative value to that of the milk basic protein fraction alone (set as 1).
The numeric value indicates mean ± standard deviation (n = 6).
"a" indicates a significant difference from the activity of the control ($p < 0.05$).

The results shown in Table 8 revealed that all the protein compositions maintained relative osteoblast proliferation activities of 1 or greater with respect to that observed for the milk basic protein fraction alone after the heating up to a temperature of 140° C. Such results demonstrate that the protein composition of the present invention is stable against an extreme heat treatment at a temperature of 140° C.

Test Example 13

A solution containing the protein composition prepared as in the Test Example 2 (containing 50 mg % milk basic protein fraction and 0.04% by weight of xanthan gum) was adjusted to have pH values of 2 to 9, respectively. Each sample (150 ml) was packed and sealed in retort pouches. As controls, solutions containing LF (lactoferrin) alone were adjusted to have pH values of 2 to 9, respectively, and each sample (150 ml) was packed and sealed in retort pouches. The solutions were heated with a retort sterilizer (first-class pressure vessel, TYPE: RCS-4CRTGN; manufactured by HISAKA WORKS, LTD.) at a temperature of 120° C. for four minutes. Each of the samples after the heating was preserved at 25° C. and was analyzed for the presence of aggregation or precipitation by visual observation and for the band pattern of the milk basic protein fraction by polyacrylamide gel electrophoresis (SDS-PAGE).

As a result, for the control samples, i.e. the solutions which contained LF alone and had been adjusted to have pH values of 2 to 9, aggregation and precipitation was observed on day 1. In contrast, for the solutions which contained the respective protein compositions and had been adjusted to have pH values of 2 to 9, no aggregation or precipitation was observed even after one month of preservation. In the analysis of the band patterns of the milk basic protein fraction by SDS-PAGE, for the solutions which contained the respective protein compositions and had been adjusted to have pH values of 2 to 9, the bands of the milk basic protein fraction were observed and no other change was observed at the initiation of preservation and even after one month of preservation. Such experimental results demonstrate that the protein composition of the present invention is also effective in a retort sterilization treatment.

Test Example 14

With 200 g of the protein composition prepared as in the Test Example 2 (containing 50 mg % milk basic protein fraction and 0.04% by weight of xanthan gum), 800 g of reconstituted skim milk powder solution (containing 3% by weight of skim milk powder) was mixed to prepare solution (1) containing a protein composition. As controls, solution (2) was prepared by mixing 200 g of the solution containing the milk basic protein fraction (50 mg % solution of the milk basic protein fraction) with 800 g of reconstituted skim milk powder solution (containing 3% by weight of skim milk powder), and 1000 g of solution (3) of reconstituted skim milk powder alone (containing 3% by weight of skim milk powder) was prepared. The individual solutions (150 ml) were packed and sealed in retort pouches. These solutions were then heated with a retort sterilizer (first-class pressure vessel, TYPE: RCS-4CRTGN; manufactured by HISAKA WORKS, LTD.) at a temperature of 120° C. for 20 minutes. As a result, the solutions (1) and (3) exhibited no aggregation or precipitation and had an excellent flavor, while the solution (2) exhibited aggregation and precipitation. Such experimental results demonstrate that the protein composition of the present invention is significantly effective in a retort sterilization treatment.

Test Example 15

The milk basic protein fraction of Reference Example Product A was dissolved in deionized water into a concentration of 100 mg % (Solution A), and 0.4% by weight of soybean polysaccharide, 0.04% by weight of xanthan gum, 0.05% by weight of tamarind gum, and 0.1% by weight of sucrose fatty acid ester as stabilizers were respectively dissolved in deionized water (Solutions B). The Solution A was mixed with each of the Solutions B by stirring with an ultrasonic disperser (ULTRA-TURRAX T-25; manufactured by IKA Japan) at 8000 rpm and at a temperature of 50° C. for three minutes to prepare a protein composition. Lactic acid or sodium hydroxide solution was then added to each of the protein compositions as pH adjusters, to prepare a sample having a pH value of 6.5. Each of the samples thus prepared was heated at a temperature of 120° C. for four minutes, and was analyzed for aggregation and precipitation by visual observation and for the degree of degradation of the protein composition by SDS-PAGE, before and after the heat treatment, in accordance with the methods in Test Example 1. The results are shown in Table 9.

TABLE 9

| Samples | Stabilizers | Visual SDS-PAGE |
|---|---|---|
| Protein composition before heating (tamarind gum) | – | ○ |
| Protein composition after heating (tamarind gum) | + | x |
| Protein composition before heating (sucrose fatty acid ester) | – | ○ |
| Protein composition after heating (sucrose fatty acid ester) | ± | x |
| Protein composition before heating (soybean polysaccharide) | – | ○ |
| Protein composition after heating (soybean polysaccharide) | – | ○ |
| Protein composition before heating (xanthan gum) | – | ○ |
| Protein composition after heating (xanthan gum) | – | ○ |

Note)
1: visual observation of aggregation and precipitation "–" indicates transparent due to no aggregation or precipitation. "± " indicates translucent, but no aggregation or precipitation. "+" indicates presence of aggregation or precipitation.
Note)
2: observation by electrophoresis (SDS-PAGE) "○" indicates observation of protein bands by SDS-PAGE. "Δ" indicates observation of slight protein bands by SDS-PAGE. "x" indicates observation of no protein band by SDS-PAGE.

The results shown in Table 9 indicate that any of the protein compositions before the heat treatment was transparent due to no aggregation or precipitation, and the bands of the milk basic protein fraction were observed. After the heat treatment, the protein composition containing soybean polysaccharide and the protein composition containing xanthan gum were transparent and the bands of the milk basic protein fraction were observed for these protein compositions. In contrast, both the protein composition containing tamarind gum and the protein composition containing sucrose fatty acid ester were translucent or exhibited aggregation or precipitation, and no band of the milk basic protein fraction was observed for these protein compositions in SDS-PAGE.

EXAMPLES

Example 1

The milk basic protein fraction of Reference Example Product B was dissolved in deionized water into a concentration of 50 mg % (Solution A, 300 g), and 0.4% by weight of soybean polysaccharide as a stabilizer was dissolved in deionized water (Solution B, 300 g). The Solutions A and B were mixed together by stirring with an ultrasonic disperser (ULTRA-TURRAX T-25; manufactured by IKA Japan) at 9500 rpm and at a temperature of 50° C. for three minutes to prepare 600 g of a protein composition of the present invention.

Example 2

The milk basic protein fraction of Reference Example Product A was dissolved in deionized water into a concentration of 40 mg % (Solution A, 10 kg), and 0.08% by weight of xanthan gum as a stabilizer was dissolved in deionized water (Solution B, 10 kg). The Solutions A and B were mixed together by stirring with a T.K. homogenizing mixer (MARK II 160 Model; manufactured by Tokushu Kika Kogyo Co., Ltd.) at 3600 rpm for 30 minutes. The resulting mixture was concentrated with a UF membrane having a molecular weight cut off of 10 kDa, to prepare 10 kg of a protein composition of the present invention.

Example 3

The milk basic protein fraction of Reference Example Product B was dissolved in deionized water into a concentration of 100 mg % (Solution A, 1000 kg), and 0.4% by weight of pectin as a stabilizer was dissolved in deionized water (Solution B, 1000 kg). The Solutions A and B were mixed together by stirring with a T. K. homogenizing mixer (MARK II 2500 Model; manufactured by Tokushu Kika Kogyo Co., Ltd.) at 3600 rpm and at a temperature of 40° C. for 40 minutes. The resulting mixture was then lyophilized to prepare 3.9 kg of a protein composition of the present invention.

Example 4

The milk basic protein fraction of Reference Example Product A was dissolved in deionized water into a concentration of 100 mg % (Solution A, 500 g), and 0.4% by weight of soybean polysaccharide as a stabilizer was dissolved in deionized water (Solution B, 500 g). The Solutions A and B were mixed together by stirring with an ultrasonic disperser (ULTRA-TURRAX T-25; manufactured by IKA Japan) at 9500 rpm and at a temperature of 40° C. for three minutes. The mixture solution was then mixed with 80 g of sorbitol, 4 g of acidulant, 4 g of flavor, 10 g of pectin, 10 g of whey protein concentrate, 2 g of calcium lactate, and 890 g of water by stirring, to prepare a protein composition of the present invention. The protein composition was packed in 200 ml cheer packs. The packs were sterilized at a temperature of 85° C. for 20 minutes, and then were sealed, to prepare 10 packs of gelled food containing the protein composition of the present invention. No precipitation or abnormal flavor was found in any of the gelled foods thus prepared.

Example 5

The milk basic protein fraction of Reference Example Product B was dissolved in deionized water into a concentration of 500 mg % (Solution A, 200 g), and 4% by weight of soybean polysaccharide as a stabilizer was dissolved in deionized water (Solution B, 200 g). A protein composition of the present invention was prepared by mixing 100 g of maltitol, 20 g of reduced sugar syrup, 2 g of acidulant, 2 g of flavor, 200 g of the Solution A, 200 g of the Solution B, and 476 g of water. The resulting protein composition was filled in 50 ml glass bottles. The bottles were sterilized at a temperature of 90° C. for 15 minutes and then were sealed, to prepare 20 bottles of beverage containing the protein composition of the present invention. No precipitation or abnormal flavor was found in any of the beverages thus prepared.

Example 6

With 0.2 kg of the protein composition prepared in the Example 2 (containing 20 mg % milk basic protein fraction and 0.04% by weight of xanthan gum), 12 kg of soybean meal, 14 kg of skim milk powder, 4 kg of soybean oil, 2 kg of corn oil, 28 kg of palm oil, 15 kg of corn starch, 9 kg of wheat flour, 2 kg of wheat bran, 9 kg of vitamin mixture, 2.8 kg of cellulose, and 2 kg of mineral mixture were mixed. The resulting mixture was sterilized at a temperature of 120° C. for four minutes, to prepare 100 kg of canine feed.

Example 7

With 3 kg of the protein composition prepared in the Example 3 (containing 50 mg % milk basic protein fraction and 0.2% by weight of pectin), 5 kg of casein, 5 kg of soybean protein, 1 kg of fish oil, 3 kg of perilla oil, 19 kg of dextrin, 6 kg of mineral mixture, 1.95 kg of vitamin mixture, 2 kg of emulsifier, 4 kg of stabilizer, and 0.05 kg of flavor were mixed. The resulting mixture was packed in 200 ml retort pouches. The retort pouches were sterilized with a retort sterilizer (first-class pressure vessel, TYPE: RCS-4CRTGN; manufactured by HISAKA WORKS, LTD.) at a temperature of 121° C. for 20 minutes, to prepare 50 kg of enteral nutrient.

The invention claimed is:

1. A thermally stable protein composition comprising:

a) a milk basic protein fraction; and b) an amount effective for thermal stabilization of the milk basic protein fraction of at least one stabilizer selected from the group consisting of soybean polysaccharides, xanthan gum, pectin, gum arabic, gum ghatti, carrageenan, locust bean gum, sodium caseinate, lecithin, and carboxymethylcellulose wherein the thermal stabilization is stability of the milk basic protein fraction after heating to 90° C. for 4 minutes at a pH from 2 to 9, and wherein the milk basic proteins do not aggregate during the heating step.

2. The protein composition according to claim 1, wherein the milk basic protein fraction has an amino acid composition containing 15% by weight or more basic amino acids.

3. The protein composition according to claim 1, wherein:

1) the milk basic protein fraction comprises several proteins each having a molecular weight within the range of 3,000 to 80,000 as determined by sodium dodecyl sulfate-polyacrylamide gel electrophoresis (SDS-PAGE);

2) the milk basic protein fraction contains 95% by weight or more proteins and the remainder comprising lipids and ash;

3) the milk basic protein fraction comprises 40% by weight or more lactoferrin and 40% by weight or more lactoperoxidase; and 4) the proteins in the milk basic protein fraction have an amino acid composition containing 15% by weight or more basic amino acids.

4. A food, beverage, feed or pharmaceutical comprising the protein composition according to claim 1.

5. A process for heat treatment of a milk basic protein Fraction comprising;

heating the composition of claim 1 to a temperature of 90° C. or higher.

6. The process for heat treatment of a milk basic protein fraction according to claim 5, wherein the milk basic protein fraction has an amino acid composition containing 15% by weight or more basic amino acids.

7. The process for heat treatment of a milk basic protein fraction according to claim 5, wherein:

1) the milk basic protein fraction contains proteins each having a molecular weight within the range of 3,000 to 80,000 as determined by sodium dodecyl sulfate-polyacrylamide gel electrophoresis (SDS-PAGE);

2) the milk basic protein fraction contains 95% by weight or more proteins and the remainder comprises lipids and ash;

3) the milk basic protein fraction are comprises 40% by weight or more lactoferrin and 40% by weight or more lactoperoxidase; and 4) the proteins in the milk basic protein fraction have an amino acid composition containing 15% by weight or more basic amino acids.

8. A food, beverage, feed, or pharmaceutical comprising the protein composition according to claim 2.

9. A food, beverage, feed or pharmaceutical comprising the protein composition according to claim 3.

10. The thermally stable protein composition according to claim 1, wherein the stabilizer is in a weight ratio to the milk basic protein fraction of 1:1 to 100:1.

11. The thermally stable protein composition according to claim 1, wherein the stabilizer is in a weight ratio to the milk basic protein fraction of 1:1 to 40:1.

12. The thermally stable protein composition according to claim 1, wherein the thermally stable protein composition can be heated to 100° C. for at least 4 minutes at a pH from 2.0 to 9.0 and not aggregate.

13. The thermally stable protein composition according to claim 1, wherein the thermally stable protein composition can be heated to 110° C. for at least 4 minutes at a pH of 2.0 to 9.0 and not aggregate.

14. The thermally stable protein composition according to claim 1, wherein the thermally stable protein composition can be heated to 120° C. for at least 4 minutes at a pH of 2.0 to 9.0 and not aggregate.

15. The thermally stable protein composition according to claim 1, wherein the thermally stable protein composition can be subjected to a pH of 5.0 to 9.0 at 110° C. for at least 4 minutes and not aggregate.

16. The thermally stable protein composition according to claim 1, wherein the thermally stable protein composition can be subjected to a pH of 6.0 to 9.0 at 110° C. for at least 4 minutes and not aggregate.

17. The thermally stable protein composition according to claim 1, wherein the thermally stable protein composition can be subjected to a pH of 7.0 to 9.0 at 110° C. for at least 4 minutes and not aggregate.

18. The thermally stable protein composition according to claim 1, wherein the thermally stable protein composition can be subjected to a pH of 8.0 to 9.0 at 110° C. for at least 4 minutes and not aggregate.

19. The thermally stable protein composition according to claim 1, wherein the thermally stable protein composition can be subjected to a pH of 9.0 at 110° C. for at least 4 minutes and not aggregate.

* * * * *

UNITED STATES PATENT AND TRADEMARK OFFICE

CERTIFICATE OF CORRECTION

PATENT NO. : 9,861,121 B2
APPLICATION NO. : 14/779647
DATED : January 9, 2018
INVENTOR(S) : H. Urazono et al.

It is certified that error appears in the above-identified patent and that said Letters Patent is hereby corrected as shown below:

At Column 21, Line 54 (Claim 4, Line 1), please change "feed" to -- feed, --.
At Column 21, Line 57 (Claim 5, Line 2), please change "Fraction" to -- fraction --.
At Column 22, Line 20 (Claim 9, Line 1), please change "feed" to -- feed, --.

Signed and Sealed this
Seventh Day of August, 2018

Andrei Iancu
*Director of the United States Patent and Trademark Office*